July 2, 1946. C. DE GROOT Plant Pat. 703
BARBERRY PLANT
Filed June 7, 1945
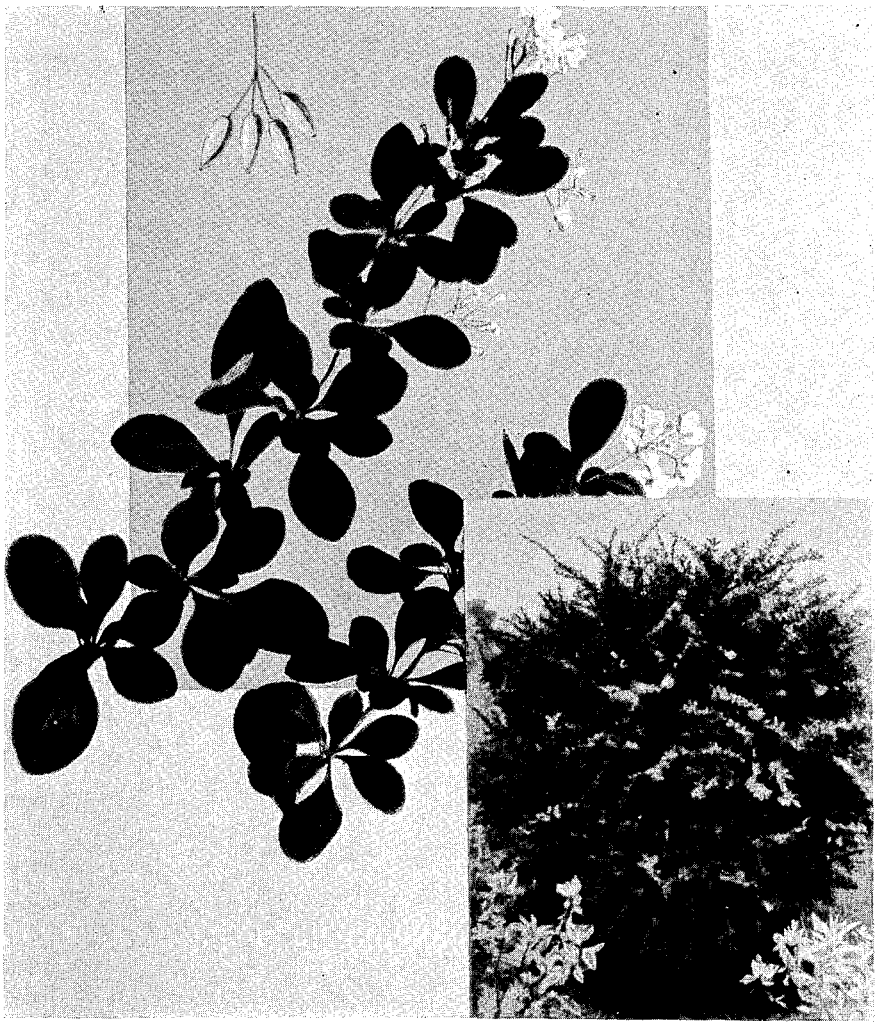
Inventor
C. De Groot
By Robert Robb
His attorney Patented July 2, 1946

Plant Pat. 703

UNITED STATES PATENT OFFICE

703

BARBERRY PLANT

Constant De Groot, Sheridan, Ontario, Canada, assignor to Jackson & Perkins Company, Newark, N. Y., a corporation of New York Application June 7, 1945, Serial No. 597,975

1 Claim. (Cl. 47—59)

The present invention relates to a new and distinct variety of barberry plant originating as a chance "Japonica" seedling.

This new variety is particularly useful not only as a hedge plant, but as an ornamental bush. For hedge purposes, it is ideal because of its quick, tall, narrow and impervious habits of growth, and as an ornamental it develops into a colorful single bush of beauty.

In the accompanying composite drawing is illustrated a specimen of its fruit, specimens of its respective mature and young foliage with blossoms, and a specimen of its dense, tall growth as a single ornamental bush plant.

This new barberry is distinguished specifically from *Barberry thunbergi,* by its rapid growth combined with the smaller foliage and spine characteristics. It is distinguishable from the species *Barberry vulgaris,* since it bushes and fills in and becomes a compact hedge. This is not the case with the vulgaris habit of growth, which is well known to be what is commonly called leggy in the trade. In the second place, this new variety has a tall narrow growth and is very amenable to trimming and remains full and compact, whereas vulgaris does not. Again, the fruit of the present variety is not as conspicuous as is that of vulgaris; in fact, it resembles very much the fruit of the japonica which is smaller than the fruit of the vulgaris.

Other features of novelty reside in the color of its foliage as hereinafter specifically set forth, and by its cluster arrangement of oblong red fruit, as clearly illustrated in the drawing.

Asexual reproduction shows that these characteristics hold true through succeeding propagations.

The following is a detailed description of this new variety, color terminology being in accord with Ridgway's Color Standard:

Parentage:

*Seedling.*—"Japonica."

Classification:

*Botanic.—Barberry thunbergi* (japonica).

(Observations made in the gardens of Jackson & Perkins Company, Newark, New York.)

Blooming habit: Blooms once—early; flowers in June.

Plant growth: Growth of plant is upright and rapid; lends itself to shearing into narrow compact hedges. Unlike *Barberry thunbergi* which needs constant attention, this holds its form much better when sheared. The upright growth is much more vigorous than *Barberry thunbergi,* the bottom branches ascending and making hedges four feet tall within a period of three years. This variety is easily maintained in narrow hedges unlike the thunbergi which must broaden a great deal more for the same height.

Color: Coloring of the foliage varies in the new growth and the old growth. The new growth is—

*Upper side.*—Victoria Lake, Plate 1.

*Under side.*—Corydalis Green, Plate 41, which changes to—

*Upper side.*—Hay's Maroon, Plate 13.

*Under side.*—Light Grape Green, Plate 41, as the foliage matures. This matured foliage is deeper than barberry known as "Red Japonica Barberry" and is quite distinct therefrom.

Leaf formation: Spatulate in clusters similar to *Barberry vulgaris;* leaves are about 1½ inches long.

*Texture.*—Leathery above and glaucescent below.

*Midrib and veins.*—Quite prominent.

Spines: The spines are simple at each leaf cluster of Russet color, Plate 15. The Russet, Plate 15, spines are similar to the thunbergi but differ from the vulgaris, which are tripartite.

Branches: Chestnut Brown, Plate 14—and upright.

Blossoms: The flowers are borne on many pendulous racemes—many flowered. Color of petals—Citron Yellow, Plate 16. The narrow sepals are a Scarlet Red, Plate 1. Flowers are not very conspicuous.

Fruit: Oblong; Nopal Red, Plate 1. Fruit remains after the foliage drops, but it is not quite as free as it is on the parents.

Hardiness: The variety is hardy in northern New York and south central Canada, and is hardier than the red form of the thunbergi.

I claim:

A new and distinct variety of barberry plant, characterized as to novelty by its habit of rapid growth, combined with the smaller foliage and spine characteristics of *Barberry thunbergi;* the color of its foliage; cluster arrangement of oblong red fruit; adaptability for hedge usage by reason of its quick, tall, narrow and impervious habits of growth; and its adaptability for usage as a single ornamental bush of vigorous, hardy and colorful growth, substantially as shown and described.

CONSTANT DE GROOT.